(12) United States Patent
Kawai et al.

(10) Patent No.: US 6,586,019 B1
(45) Date of Patent: Jul. 1, 2003

(54) DEODORANT

(75) Inventors: Toshikazu Kawai, Kanagawa (JP);
Hitoshi Nakada, Okayama (JP);
Tadashi Ebashi, Chiba (JP)

(73) Assignee: Mitsui Sugar Co., Ltd., Tokyo (JP)

( * ) Notice: Subject to any disclaimer, the term of this patent is extended or adjusted under 35 U.S.C. 154(b) by 0 days.

(21) Appl. No.: 09/269,363

(22) PCT Filed: Sep. 24, 1997

(86) PCT No.: PCT/JP97/03389

§ 371 (c)(1),
(2), (4) Date: May 25, 1999

(87) PCT Pub. No.: WO98/13075

PCT Pub. Date: Apr. 2, 1998

(30) Foreign Application Priority Data

Sep. 24, 1996 (JP) .............................................. 8-271305

(51) Int. Cl.[7] .............................................. A61K 35/78
(52) U.S. Cl. .................... 424/750; 424/725; 424/65; 424/76.1; 127/55; 127/46.1
(58) Field of Search ................ 424/195.1, 65, 424/76.1, 725, 750; 127/55, 46.1

(56) References Cited

U.S. PATENT DOCUMENTS

| 4,101,338 A | * | 7/1978 | Rapaport et al. .............. 127/46 |
| 4,426,232 A | * | 1/1984 | Neuzil et al. ............... 127/46.3 |
| 5,009,887 A | * | 4/1991 | Iwahashi ................... 424/76.1 |

FOREIGN PATENT DOCUMENTS

| JP | 60136506 A | | 7/1985 |
| JP | 60214726 A | | 10/1985 |
| JP | 63-40556 | * | 2/1988 |
| JP | 1-119255 | * | 5/1989 |
| JP | 02277456 A | | 11/1990 |
| JP | 02284997 A | | 11/1990 |
| JP | 0302151 A | | 1/1991 |
| JP | 05038358 A | | 2/1993 |
| JP | 05317397 A | | 12/1993 |
| JP | 06190027 A | | 7/1994 |
| JP | 07033636 A | | 2/1995 |
| JP | 08266247 A | | 10/1996 |
| WO | WO 94/17213 | | 4/1994 |

OTHER PUBLICATIONS

XP–002224718 (Aug. 22, 1986) Abstract.
JP Application Laid–Open No. 48–23946, Laying–Open Date: Mar. 23, 1973, Claim.
JP Application Laid–Open No. 50–31052, Laying–Open Date: Mar. 27, 1975, Claim.
JP Application Laid–Open No. 60–185558, Laying–Open Date: Sep. 21, 1985, Claims.
JP Application Laid–Open No. 60–207664, Laying–Open Date: Oct. 19, 1985, Claims.
JP Application Laid–Open No. 61–87562, Laying–Open Date: May 2, 1986, Claims.
JP Application Laid–Open No. 61–206448, Laying–Open Date: Sep. 12, 1986, Claims.
JP Application Laid–Open No. 62–152463, Laying–Open Date: Jul. 7, 1987, Claims.
JP Application Laid–Open No. 62–181048, Laying–Open Date: Aug. 8, 1987, Claims.

* cited by examiner

Primary Examiner—Francisco Prats
(74) Attorney, Agent, or Firm—Pitney, Hardin, Kipp & Szuch LLP (57) ABSTRACT

The present deodorizing substance is obtained by treating a raw material selected from sugar cane juice and sugar cane-derived molasses by column chromatography, and characterized in that the substance is a fraction obtained by passing the aforesaid raw material through a column packed with a synthetic adsorbent as a fixed carrier and eluting ingredients adsorbed on said synthetic adsorbent with a solvent selected from water, methanol, ethanol and a mixture thereof. The present deodorizing substance is inexpensive and has high safety. It may be used widely in foods and environmental protection fields.

9 Claims, 2 Drawing Sheets

DEODORANT

FIELD OF THE INVENTION

The present invention is related to a deodorizing substance effective for deodorizing a bad smell such as methylmercaptan, trimethylamine, ammonia, more specifically to the aforesaid deodorizing substance which may be used for applications, for instance, in foods, feeds, sanitary goods, table luxuries, medicines and quasi-drugs.

PRIOR ART

Recently, men as well as women have increasingly been interested in eliminating a foul breath or a body smell with the increasing standard of living. Many products declaring a deodorant effect have been commercially available, such as those for preventing the foul breath or the body smell, for example, candies or chewing gum for preventing the foul breath, and those for removing a smell of, for example, insoles. In addition, the need to deodorant goods has spread among people of a wide range of ages and, therefore, their market has expanded year by year. Further, many deodorizing substances have been commercially available to be used for improving environments, for example, in rooms, in cars, in refrigerators, in toilet rooms, in house of domestic animals, in fish tanks or in factories, or for eliminating bad smells generated from domestic wastes or industrial wastes.

As a mean or a mechanism for preventing the generation of unpleasant smells or for eliminating generated unpleasant smells, there has been known sensuous deodorization (a method for masking the unpleasant smells with aromatic substances such as perfume); physical deodorization (a method for diluting or eliminating the unpleasant smells by, for example, adsorbing them onto active carbon, including them in cyclodextrin, ventilation or diffusion); chemical deodorization (a method for deodorizing the unpleasant smells by chemical reactions such as neutralization, addition, condensation or oxidation); and biological deodorization (a method for preventing the generation of the unpleasant smells by killing bacteria to prevent putrefaction). Deodorizing agents according to the aforesaid deodorizing mechanisms have been developed.

Among the deodorizing substances, those used in the field of foods are required to be safe for a human body when eaten or drunk. To this end, researches on deodorizing substances have centered on those derived from plants which have been used for foods. For example, the following substances are said to be effective for deodorization: extracts of green tea (Japanese Patent Application Laid-Open No. Sho-60-185558/1985), extracts of red beet, cacao, coffee and parsley (Japanese Patent Application Laid-Open No. Sho-60-207664/1985), Perilla extracts (Japanese Patent Application Laid-Open No. Sho-60-214726/1985), persimmon extracts (Japanese Patent Application Laid-Open No. Sho-61-87562/1986), butterbur extracts (Japanese Patent Application Laid-Open No. Sho-61-206448/1986), seaweed extracts (Japanese Patent Application Laid-Open No. Sho-62-152463/1987), finely divided Ganoderma, "Mannentake" (Japanese Patent Application Laid-Open No. Sho-62-181048/1987), Angelica acutiloba (Umbelliferae) extracts (Japanese Patent Application Laid-Open No. Hei-5-317397/1993), tannin fractions of tea leaf extracts (Japanese Patent Application Laid-Open No. Hei-2-284997/1990), Umbelliferae extracts (Japanese Patent Application Laid-Open No. Hei-6-190027/1994), mugwort extracts (Japanese Patent Application Laid-Open No. Hei-7-33636/1995) and mushroom extracts (Japanese Patent Application Laid-Open No. Hei-2-277456/1990 and Hei-5-38358/1993).

In addition to the aforesaid substances, the following substances are known as deodorizing substances usable in the field of foods: dimethylaminosulfonate, glucosamine (Japanese Patent Application Laid-Open No. Sho-48-23946/1973), cyclodextrin (Japanese Patent Application Laid-Open No. Sho-55-122700/1980), organic acids such as L-ascorbic acid, benzoic acid, gluconic acid, foric acid and nicotinic acid and salts thereof (Japanese Patent Application Laid-Open No. Sho-60-136506/1985).

The aforesaid deodorizing substances which are said to have high safety have a problem that they have a taste such as a bitter taste, a strong odor or a peculiar color. Because those substances have the possibility to influence a taste, flavor or color of the food when used as a deodorizing substance in an effective amount, types of food to which they can be applied are limited. Moreover, some substances have problems such as narrow selectivity in a deodorizing effect to bad smell substances or a weak deodorizing effect. Otherwise, the deodorizing substances derived from natural origins have the following problems: because their raw materials themselves are expensive, or their extraction cost is high, the products are generally expensive and, therefore, prices of the foods or medicines to which they are applied are higher. In addition, some substances have problems in their quality such as safety or preservative quality when used in foods.

DISCLOSURE OF THE INVENTION

A purpose of the invention is to provide a deodorizing substance which is inexpensive, have high safety and may be used widely in the fields of foods and environmental protection.

The present invention provides a deodorizing substance obtained by treating a raw material selected from sugar cane juice and sugar cane-derived molasses by column chromatography, characterized in that the substance is a fraction obtained by passing the aforesaid raw material through a column packed with a synthetic adsorbent as a fixed carrier and eluting ingredients adsorbed on said synthetic adsorbent with a solvent selected from water, methanol, ethanol and a mixture thereof.

BEST EMBODIMENTS FOR THE PRACTICE OF THE INVENTION

In the invention, the terms "sugar cane juice" mean mill juice obtained by crushing sugar cane, extracted juice obtained by extracting sugar cane, clarified juice obtained after treatment with lime in a sugar mill, concentrated juice, juice from a resin tower in a sugar refinery, or a reformed extract which is obtained as follows: sugar cane is extracted with a solvent used widely in extracting methods for plant-derived ingredients, after which the extract is concentrated, dried up and re-dissolved in water. The aforesaid solvent includes, for example, alcohols such as methanol and ethanol; ketones such as acetone; and esters of acetic acid such as methyl acetate and ethyl acetate. These solvents may be used alone or as a combination of these. In the case of the alcohols or ketones, they may be used as a combination with water.

The terms "sugar cane-derived molasses" mean a molasses part remaining after sugars are removed from sugar cane juice by centrifugation, for example, first Siroshita, second Siroshita and waste molasses in a sugar mill and affination syrup, brown liquor and refinery waste molasses in a sugar refinery and the like. Particularly, waste molasses and refinery waste molasses mean a molasses part remaining after a large part of sugars is removed from sugar cane juice and is the part which is obtained finally in a sugar refinery and in which no more sugar can be recovered economically.

The present deodorizing substance is obtained by treating the aforesaid sugar cane juice and/or molasses by column chromatography using a fixed carrier. The aforesaid sugar cane juice or molasses as such or after diluted with water to a desired concentration is treated in a column packed with the fixed carrier. It is preferred that the sugar cane juice and/or molasses is subjected to filtration before treated by column chromatography. The filtration manner is not restricted to particular one. Use may be preferably made of various means used widely in the food industry such as screen filtration, diatomaceous earth filtration, precision filtration and ultrafiltration.

As the fixed carrier, a synthetic adsorbent is used. As the synthetic adsorbent, use may be preferably made of organic resins such as aromatic resins, acrylic acid type methacrylic resins and acrylonitrile aliphatic resins. More preferable are the aromatic resins, particularly unsubstituted aromatic resins. As the synthetic adsorbent, aromatic resins, for example, styrene-divinylbenzene resin may be used. As the aromatic resin, use may be made of, for example, such as aromatic resins having hydrophobic substituents, unsubstituted aromatic resins and aromatic resins obtained by subjecting unsubstituted type aromatic resins to a particular treatment. More preferably, use may be made of the aromatic resins obtained by subjecting the unsubstituted type aromatic resins to a particular treatment. These synthetic adsorbents are commercially available. Mention may be made of, for example, Diaion® series, such as HP-10, HP-20, HP-21, HP-30, HP-40 and HP-50 (trade names, ex Mitsubishi Chemicals Inc.: these are unsubstituted aromatic resins), SP-825, SP-800, SP-850 and SP-875 (trade names, ex Mitsubishi Chemicals Inc.: these are aromatic resins obtained by subjecting the unsubstituted type aromatic resins to a particular treatment,); SP-900 (trade name, ex Mitsubishi Chemicals Inc., aromatic resin), AMBERLITE® series such as XAD-2, XAD-4, XAD-16 and XAD-2000 (trade names, ex Organo Corporation: these are aromatic resins); Diaion® series such as SP-205, SP-206 and SP-207 (trade names, ex Mitsubishi Chemicals Inc.: these are aromatic resins having hydrophobic substituents), HP-2MG and EX-0021 (trade names, ex Mitsubishi Chemicals Inc.: these are aromatic resins having hydrophobic substituents), AMBERLITE® series such as XAD-7 and XAD-8 (trade names, ex Organo Corporation: these are aromatic resins having hydrophobic substituents), Diaion® series such as HP1MG and HP2MG (trade names, ex Mitsubishi Chemicals Inc.: these are acrylic acid type methacrylic resins), Sephadex® series such as LH20 and LH60 (trade names, ex Pharmacia Biotech Inc.: these are cross-linked dextran derivatives) and the like. Among these, SP-850 is particularly preferable.

An amount of the fixed carrier varies depending upon a size of column, a type of solvent and a type of the fixed carrier. A preferable amount is 0.01 to 5 times, as a wet volume, as large as a solid content of the raw material selected from sugar cane juice and molasses.

Ingredients having a deodorizing effect in the raw material are adsorbed on the fixed carrier and a most part of sugars flow out to be removed by passing the raw material selected from sugar cane juice and molasses through the aforesaid column.

The ingredients adsorbed on the fixed carrier are eluted with a solvent. In order to efficiently elute the ingredients having a deodorizing activity, it is preferred to wash the column sufficiently with water to remove the remaining sugars and salts before the elution, whereby the intended deodorizing substances which are still adsorbed may be recovered efficiently. The elution solvent is selected from water, methanol, ethanol and a mixture thereof. Preference is given to a mixed solvent of water with methanol, particularly an ethanol-water mixed solvent, more particularly a mixed solvent of ethanol and water in a volume ratio of 50/50 to 60/40 because the intended deodorizing substances may be eluted efficiently at room temperature. In addition, elevation of a column temperature allows one to decrease the ethanol ratio in the ethanol-water mixed solvent. When a column temperature is 50 to 120° C., the intended deodorizing substances may be eluted efficiently with water alone. Here, a pressure in the column is atmospheric or higher. While the ingredients having a deodorizing activity are thus present in the fractions eluted with the aforesaid solvent, the sugars remaining in the column elute first or flow out. Therefore, it is preferred to recover fractions after the sugars (particularly sucrose, glucose and fructose) have almost eluted. An elution rate varies depending upon a size of column, a type of solvent and a type of the fixed carrier, and is not restricted to particular value, but preferably, $SV=0.1$ to 10 $hour^{-1}$, wherein SV is a space velocity representing how many times volume of a liquid as much as the resin volume is passed per hour.

The present deodorizing substance may be obtained, particularly, as follows. That is, a raw material is passed through a column packed with a unsubstituted aromatic resin having a wet volume 0.01 to 5 times as much as a solid content of the raw material at a column temperature of 60 to 97° C. The ingredients adsorbed in the column are then eluted at a column temperature of 20 to 40° C. with a mixed solvent of ethanol and water in a volume ratio of 50/50 to 60/40 and the fractions are recovered in a range where a volume of the eluate collected since the start of the elution with the ethanol-water mixed solvent is at most 4 times as much as the wet volume of the aforesaid resin.

The fractions thus recovered, which have a deodorizing activity, are combined and concentrated in a conventional manner such as distillation under reduced pressure or lyophilization to obtain the present deodorizing substance. The deodorizing substance thus obtained may be stored in a form of liquid concentrated to a solid content of at least 60% or powder. Cold storage is preferable, particularly, in the case of the liquid.

The present deodorizing substance preferably has a sugar content of not more than 50% by weight, more preferably not more than 20% by weight, particularly not more than 5% by weight, based on the solid content. In this specification, "sugar" means sucrose, glucose and fructose. A sugar content means the total amount of these sugars contained. If the sugar content is too high, the applications are restricted because of the sweetness of the sugars; when used in sugar-free functional foods, a high sugar content is a problem; and, moreover, because a ratio of the effective ingredients for deodorization in the deodorizing substance is small, the deodorizing effect per solid content is lower. In general, the sugars may be contained in an amount of at least 0.1% by weight. A sugar content in the deodorizing substance treated with a fixed carrier may be detected by high performance liquid chromatography. However, thin layer chromatography can not detect it in some cases, depending upon concentrations of sugars.

The present deodorizing substance may further be purified. For example, purification by chromatography with a fixed carrier and/or liquid-liquid partition may be used. As the purification by chromatography with a fixed carrier, mention maybe made of, for instance, chromatography of adsorption type, partition type or molecular sieve using, for example, a synthetic adsorbent or an ion exchange resin. As the liquid-liquid partition, mention may be made of a method by a separating funnel or a method by countercurrent partition or liquid-drop countercurrent chromatography. Various purification methods may be used in any order and in any combination. The same purification may be repeated plural times. Preference is given to a combination of the chromatography with a fixed carrier with liquid-liquid partition. Purification by partition type chromatography using an ion exchange resin is also preferable.

In the adsorption type chromatography, use may be made of, for example, the synthetic adsorbents and the elution solvents therefor or the ion exchange resins described above. Either cation or anion exchange resins may be used. As a commercially available ion exchange resin, mention is made of, for example, AMBERLITE® series cation exchange resin such as CG-4000, CG-5000, CG-6000 and CG-8000 (trade names, ex Organo Corporation: these have a sulfonate group as a functional group); IR-116, IR-118, IR-120, IR-122 and IR-124 (trade names, ex Organo Corporation: these have a sulfonate group as a functional group); XT-1007, XT-1009 and XT-1002 (trade names, ex Organo Corporation: these have a sulfonate group as a functional group); and a weakly basic anion exchange resin such as OPTIPORE-XUS 40285.00 and OPTIPORE-XUS 40390.00 (trade names, ex Dow Chemical Inc.: these have a tertiary amine group as a functional group). When the ion exchange resin is used, water is preferably used as an elution solvent, and a column temperature of 50 to 120° C. and atmospheric or higher pressure in the column are preferable. Besides the synthetic adsorbents and ion exchange resins, use may be made of other adsorbents such as silica gel, active alumina, active carbon, active clay and reversed phase silica gel as a solid carrier.

The ion exchange resins and the elution solvents therefor mentioned above may be used as a fixed carrier also in the partition type chromatography. Sephadex® LH-20 and LH-60, trade names, ex Pharmacia Biotech Inc., may also be used. As a moving phase, use is made of a solvent selected from, for instance, ethanol, methanol, water and acetone.

In the molecular sieve chromatography or gel filtration chromatography, Sephadex® LH-20 and LH-60, trade names, ex Pharmacia Biotech Inc., mentioned above, may also be used as a fixed carrier. As an elution solvent, use is made of a solvent selected from, for instance, ethanol, methanol, water and acetone.

The eluted fractions having a deodorizing activity obtained by the aforesaid chromatography may be concentrated by the aforesaid conventional means.

In the liquid-liquid partition, use is made of water which dissolves the present deodorizing substances obtained above and a hydrophobic solvent as an extraction solvent. As the hydrophobic solvent, mention is made of organic solvents, for example, alcohols having 3 to 5 carbon atoms such as isopropyl alcohol, butanol (saturated with water), isoamyl alcohol; carbon chlorides such as chloroform and methylene chloride; and esters of acetic acid such as ethyl acetate and n-propyl acetate.

The countercurrent chromatography is liquid-liquid partition chromatography using no fixed carrier. Liquid, water, as a fixed phase is divided into many partition units which mix hardly with each other, through which the liquid (the aforesaid hydrophobic solvent) is passed as a moving phase. During the passage of the moving phase, partition proceeds efficiently in each unit with as less effusion of the moving phase as possible. This method gives the same effect as attained in multiple liquid-liquid partitions with a separating funnel.

The substances having strong deodorizing activity per unit solid content in the present deodorizing substances are recovered in a hydrophobic solvent. After liquid-liquid partition, the hydrophobic solvent parts are combined and concentrated to obtain the intended substances. Substances having a lower deodorizing activity than that of the aforesaid substances are mostly recovered in a water-soluble solvent. After liquid-liquid partition, the water-soluble solvent parts are combined and concentrated to obtain these substances. The concentration may be carried out by the aforesaid conventional means.

The present deodorizing substances may affect a bad smell substance such as methylmercaptan, trimethylamine and ammonia to eliminate or greatly decrease the bad smell.

The present deodorizing substance obtained by column chromatography with a fixed carrier may be added to objective substances in an amount of 0.01 to 2%. Therefore, they less impair the original color, odor and taste of the objective substance, compared to the prior art deodorizing agents. Particularly, the substances having a deodorizing activity recovered by the liquid-liquid partition are less colored and have a faint good smell derived from sugar cane and a faint mild taste. Consequently, when added to various substances, the present deodorizing substance does not impair their original color, odor and taste. From the above, it is presumed that the deodorizing effect of the present deodorizing substance to the aforesaid bad smell substances is not sensuous deodorization by a masking effect against a stronger smell, but chemical or physical deodorization. Ingredients in the present deodorizing substance are not clarified. Although it is unclear what components are contained in the present deodorizing substance, it is presumed that many organic acids, flavone compounds, phenol compounds and unsaturated aldehyde compounds, which are contained in sugar cane juice or molasses, may be contained and, therefore, the deodorization occurs based on addition, neutralization or clathrate reaction of these compounds with the bad smell substances. Accordingly, this deodorizing effect is different in mechanism from the prior art deodorization caused by masking with a stronger smell of non-centrifugal sugar (kokuto), etc. In addition, non-centrifugal sugar (kokuto) has not been recognized to have a deodorizing effect to methylmercaptan. Moreover, when non-centrifugal sugar (kokuto) is used only for its deodorizing effect, it is necessary to use a very large amount of non-centrifugal sugar (kokuto). Therefore, non-centrifugal sugar (kokuto) is not practical as a deodorizing agent.

The present deodorizing substance may be prepared inexpensively because it may be obtained easily in simple apparatus in a usual raw cane sugar preparation line or a purified cane sugar preparation line in a sugar mill or a sugar refinery, respectively. Therefore, the present invention does not need equipment for complicated collection and extraction treatment of raw material and the treatment of the waste after the extraction, which are all needed to extract deodorizing ingredients from natural materials as in the prior art. As a result, the present invention needs very little investment in equipment. In addition, the removal of impurities from molasses gives an increased recovery of sugar in the sugar preparation, which is advantageous in industry. In addition, the removal of impurities is also useful from the point of view of decreasing waste (waste molasses) occurring in the preparation of sugar and further recycling the waste.

Because the present deodorizing substance is derived from sugar cane, it is suitable for food and safe. It has good processing properties and physical properties and is easily handled. In addition, it has good preservative quality.

The present deodorizing substance may be used as a main component of various deodorizing agents. Application fields, may include foods such as confectionery, soft drinks, functional seasonings and health foods; feeds such as pet foods; sanitary goods such as tooth paste, body smell-preventing agents, shampoos, soap, detergents, cleaning goods, deodorant agents, sweat-controlling agents, bath agents, skin lotions and menstrual goods; medicines such as deodorizing agents for excretions by improving intestinal environment and application to foods and drinks for patients in order to improve sanitary condition at hospitals; quasi-drugs such as agents for preventing foul breath, mouse refrigerants and nutrition supplements; cigarette filters; deodorizing agents for ash trays and insoles.

The application of the present deodorizing substance to deodorizing agents is possible in various forms such as solid, liquid or aerosol form.

The present invention will be described more specifically in the following Examples, but the present invention shall not be restricted to these Examples.

EXAMPLES

Hereinafter, percentage is % by weight, unless otherwise indicated. Sugars mean sucrose, glucose and fructose. These sugars were detected by thin layer chromatography in comparison with standard substances (sucrose, glucose and fructose). Conditions in the thin layer chromatography are as follows: plate, TLC plates silica gel 60 $F_{254}$ precoated, ex Merck Company; developing solvent, chloroform: methanol: water=65:37:9 (volume ratio); and color coupler, 1% vaniline/50% sulfuric acid aqueous solution.

Sugars were quantitatively determined by an internal standard method using high-performance liquid chromatography in comparison with the standard substances (sucrose, glucose and fructose) and then the total amount of sucrose, glucose and fructose were determined. Conditions in the high-performance liquid chromatography were as follows: column of ERC-NH-1171, ex Erma Optical Works Company; flow rate of 1.0 ml/min.; temperature of 20° C.; solvent, acetonitrile: water=80:20 (volume ratio); detector, RI-8010, ex Tosoh Company; internal standard, glycerol, ex Wako Pure Chemical Industries Company; and chromatography recorder, SC-8020, ex Tosoh Company.

Example 1
(1) Separation of a Deodorizing Substance

Six hundreds liters of a sugar cane juice (solid content of 18.8%) obtained in a sugar preparation process in a sugar mill in Thailand were heated to 80° C. with a juice heater and then filtered through a tubular type ultrafiltration membrane (Daicel Chemical Industries Ltd., type MH-25, an effective membrane area of 2 m²×3 tubes, and a fractionating molecular weight of 100,000). Fifteen liters of a synthetic adsorbent (SP-850: trade name, ex Mitsubishi Chemical Corporation) were packed in a column with a water jacket (column size: an inner diameter of 17.0 cm and a height of 100 cm). The aforesaid sugar cane juice after filtered was passed through the column at a flow rate of 30 liters/hour (Space Velocity=2 $hour^{-1}$). During the passage of the sugar cane juice, water at 80° C. was always circulated in the water jacket. Next, 45 liters of distilled water were passed through the column at a flow rate of 30 liters/hour to wash the column. Subsequently, 45 liters of a 55% ethanol aqueous solution (ethanol/water=55/45, volume ratio) were passed through the column at a flow rate of 30 liters/hour (SV=2 $hour^{-1}$) to elute the ingredients adsorbed on the synthetic adsorbent. During the passage of the eluting solvent, water at 25° C. was always circulated in the water jacket. After the fractions eluted from the column were concentrated using a concentrating machine to an about 20-fold concentration under reduced pressure, the concentrate was lyophilized overnight to obtain 655 g of liver brown powder (I).

Quantitative determination of sugars on the powder (I) gave 3.7%.

(2) Purification (A) of a Deodorizing Substance (Purification of a Deodorizing Substance by Liquid-liquid Partition)

One hundred milliliters of distilled water were added to 40 g of the powder (I) obtained in (1) above to dissolve it. The solution was adjusted to pH 7.0 with a 2N sodium hydroxide solution, to which 100 ml of ethyl acetate were then added. After the solution was shaken vigorously in a separating funnel, it was permitted to stand for 30 minutes and then an upper layer, ethyl acetate layer, was taken out. The lower layer, water layer, was further extracted with 100 ml of ethyl acetate. This extraction operation was repeated another 3 times. The ethyl acetate layers obtained were combined and concentrated with a concentrating machine under reduced pressure and then lyophilized overnight to obtain 2.2 g of yellowish orange powder (II).

Quantitative determination of sugars on the powder (II) gave 0.4%.

(3) Purification (B) of a Deodorizing Substance (Purification of a Deodorizing Substance by Partition Chromatography with an Ion Exchange Resin)

Figure 1:
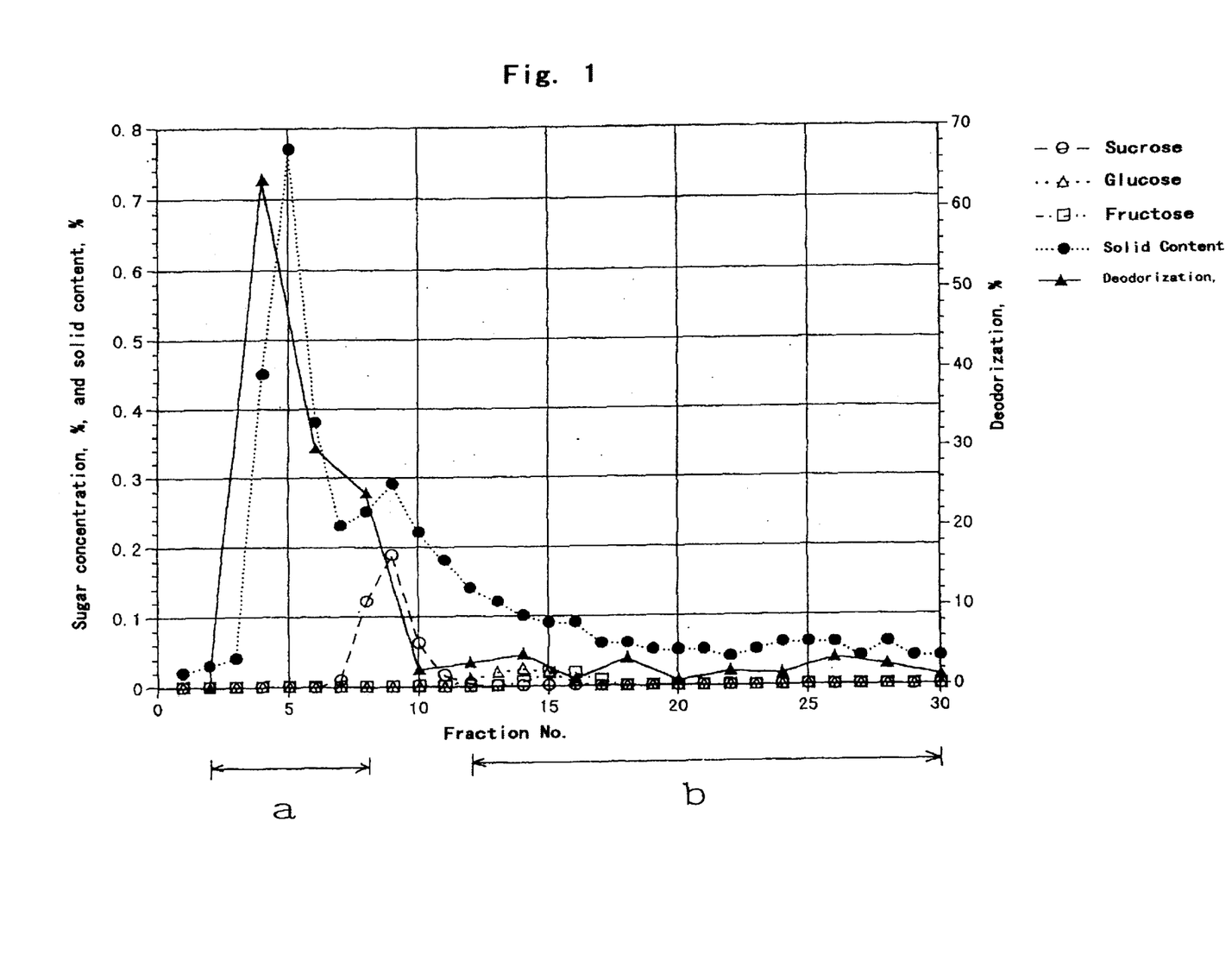
FIG. 1 shows elution patterns of partition column chromatography using an ion exchange resin in Purification (B) in Example 1 (3).

175 ml of distilled water were added to 75 g of the powder (I) obtained in (1) above to prepare a solution having a solid content of about 30%. Next, 5 liters of Amberlight CG-6000 (Na type, ex Organo Inc.) were packed in a column (column size: an inner diameter of 4.5 cm and a height of 315 cm) with a water jacket. The aforesaid solution was passed through the column. Water at 80° C. was always circulated in the water jacket. Distilled water was used as a solvent for a moving phase and a flow rate was set to 2.5 liters/hour (SV=0.5 $hour^{-1}$). The liquid eluted from the column was collected in a volume of 100 ml per fraction. Sugar determination on the fractions eluted from the column was carried out and the fractions (a) and (b) were recovered before and after the elution of sucrose, glucose and fructose, respectively. The elution pattern was as shown in FIG. 1. Each of the collected fractions (a) and (b) was concentrated with a concentrating machine under reduced pressure and then lyophilized overnight. 18.8 g of brown powder (III-1) were obtained from the earlier fractions (a) and 6.1 g of yellow powder (III-2) from the later fractions (b).

Quantitative determination of sugars on the powders (III-1) and (III-2) gave 0.1% and 0.3%, respectively.

In FIG. 1, the deodorization was determined as follows.

A 0.05% solution of methylmercaptan in benzene was provided as a bad smell solution. An aqueous 3% solution of the powder obtained by lyophilizing each fraction was adjusted to pH 7.0 with 2N sodium hydroxide. The solution thus obtained was used as a sample solution.

Each 0.1 ml of the aforesaid bad smell solution and 1 ml of the sample solution were put in a vial having a volume of 1.5 ml, which was then sealed. As a reference, the same volume of distilled water instead of the sample solution was put in a vial, which was then sealed. After stirred by a touch mixer for 20 seconds, the whole amount was put in a 300 ml-volume Erlenmeyer flask, which was then sealed tightly with parafilm®. After the flask was incubated at 30° C. for one hour to attain a saturated state, a gas concentration in the head space was determined using a gas detector tubes for the detection of a bad smell (for methylmercaptan, No. 71, ex Gastec Company). A bad smell removal, i.e. deodorization, is obtained as a ratio in percentage of the decrease in the gas concentration to the gas concentration in the reference (distilled water).

Example 2

Figure 2:
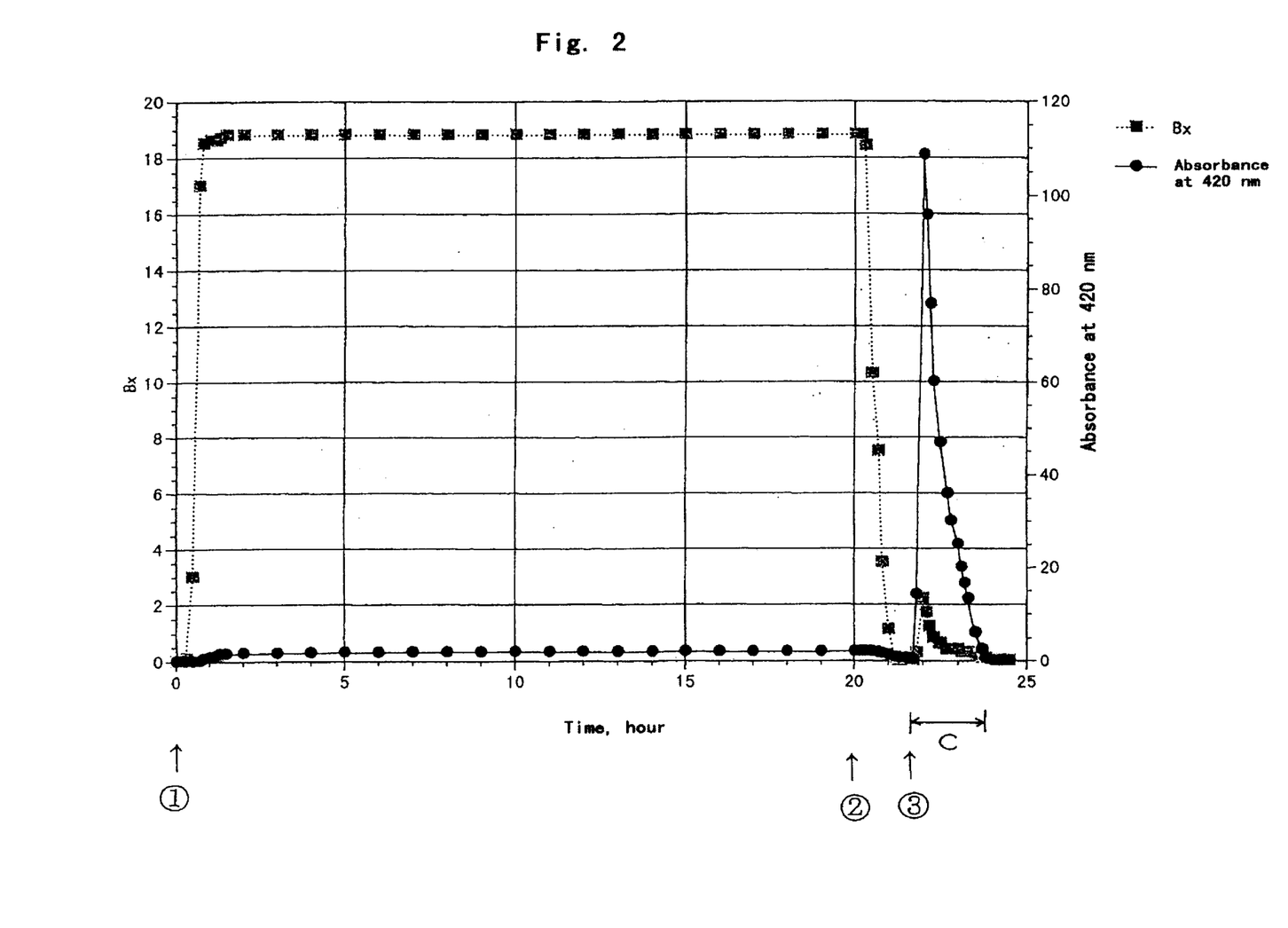
FIG. 2 shows elution patterns of adsorption column chromatography in Example 2.

1950 liters of a clarified juice (solid content of 18.7%) which was obtained by treating a sugar cane juice with lime in a sugar preparation process in a sugar mill in Thailand were heated to 80° C. with a juice heater and then filtered through three cartridge filters (ex Advantec, cotton wind cartridge filter, type TCW-100-CSD). Forty five liters of a synthetic adsorbent (SP-850; trade name, ex Mitsubishi Chemical Company) were packed in a column with a water jacket (column size: an inner diameter of 26.0 cm and a height of 120 cm). The aforesaid clarified juice after filtered was passed through the column at a flow rate of 90 liters/hour (SV=2.0 hour$^{-1}$). During the passage of the clarified juice, water at 65° C. was always circulated in the water jacket. Next, 135 liters of ion exchanged water were passed through the column at a flow rate of 90 liters/hour (SV=2.0 hour$^{-1}$) to wash the column. Sugar determination was carried out on the fractions eluted from the column after the washing with ion exchanged water. It was confirmed that Bx was about zero on a Handref brix meter (ex Atago Company, type N-1E). After that, as an eluting solvent, a 55% ethanol aqueous solution (ethanol/water=55/45, volume ratio) was passed through the column at a flow rate of 90 liters/hour (SV=2.0 hour$^{1}$-) to elute the ingredients adsorbed on the synthetic adsorbent. During the passage of the eluting solvent, water at 25° C. was always circulated in the water jacket. The liquid eluted from the column was collected in a volume of 15 liters per fraction. The elution pattern was as shown in FIG. 2, wherein (1): a starting point of passing the sugar cane juice, (2): a starting point of the washing with ion exchanged water, (3): a starting point of the elution with the 55% ethanol aqueous solution, and Bx: the solid content determined with a refractometer for Brix determination. The fractions eluted with the 55% ethanol aqueous solution from the column ((c) in FIG. 2) were concentrated with a concentrating machine under reduced pressure and then lyophilized overnight to obtain 670 g of brown powder (IV).

Quantitative determination of sugars on the powder (IV) gave 0.8%.

Testing Example 1

The effect of deodorizing a fish smell was tested using the powders (I) and (II) obtained in Example 1. 500 g of bony parts of an oceanic bonito were boiled in 1000 ml of water for 15 minutes, cooled and then filtered with a Toyo filter No.2. The filtrate was used as a fish smell solution. 1 ml of a 10% aqueous solution of the aforesaid powder and 9 ml of the aforesaid fish smell solution were put in a 50 ml-volume vial, which was then sealed. After 1 hour, the smell was examined. In a reference, the same volume of distilled water was used instead of the aforesaid solution of the powder. A sensory test was carried out by 15 professional panelists A to O with 5-level rating as indicated in Table 1 below. The results are as shown in Table 2.

TABLE 1

| Level in the Rating | Evaluation Standards |
| --- | --- |
| 0 | almost no detectable smell |
| 1 | barely detectable smell |
| 2 | immediately detectable smell |
| 3 | strong, bad smell |
| 4 | very strong, bad smell |

TABLE 2

| | Evaluation | | | | | | | | | | | | | | | |
| | Panelists | | | | | | | | | | | | | | | |
| Sample | A | B | C | D | E | F | G | H | I | J | K | L | M | N | O | Average |
| Powder (I) | 0 | 0 | 1 | 1 | 1 | 1 | 1 | 0 | 1 | 1 | 0 | 1 | 1 | 1 | 1 | 0.6 |
| Powder (II) | 1 | 1 | 0 | 1 | 1 | 0 | 1 | 1 | 1 | 0 | 0 | 1 | 1 | 2 | 1 | 0.8 |
| Reference | 3 | 4 | 3 | 3 | 3 | 3 | 3 | 4 | 3 | 3 | 3 | 4 | 3 | 3 | 4 | 3.3 |

From Table 2, it is seen that the fish smell was removed in the fish smell solution to which the present deodorizing substance was added.

Testing Example 2

A deodorization test for methylmercaptan was carried out using the powders (I), (II), (III-1) and (III-2) obtained in Example 1 and the powder (IV) obtained in Example 2. One ml of 0.1 ppm methylmercaptan was put in a 30 ml vial, to which was added 1 ml of an aqueous 3% solution of the aforesaid powder which solution had been adjusted to pH 7.0 with 2N sodium hydroxide in advance. The vial was sealed and then shaken well. After incubated at 25° C. for 15 minutes, the vial was opened and a sensory test for the smell was carried out. In a reference, the same volume of distilled water was put instead of the sample solution in a vial. The sensory test was carried out by 15 professional panelists A to O with 5-level rating as indicated in Table 1 above. The results are as shown in Table 3.

TABLE 3

| Sample | Evaluation Panelists | | | | | | | | | | | | | | | Average |
|---|---|---|---|---|---|---|---|---|---|---|---|---|---|---|---|---|
| | A | B | C | D | E | F | G | H | I | J | K | L | M | N | O | |
| Powder (I) | 1 | 1 | 2 | 1 | 1 | 1 | 1 | 1 | 2 | 1 | 1 | 1 | 1 | 2 | 1 | 1.2 |
| Powder (II) | 0 | 0 | 1 | 0 | 0 | 0 | 0 | 0 | 1 | 0 | 0 | 1 | 0 | 0 | 0 | 0.2 |
| Powder (III-1) | 1 | 1 | 1 | 1 | 0 | 1 | 1 | 0 | 0 | 1 | 1 | 1 | 1 | 1 | 1 | 0.8 |
| Powder (III-2) | 2 | 3 | 3 | 2 | 3 | 3 | 2 | 3 | 3 | 2 | 2 | 3 | 2 | 2 | 3 | 2.5 |
| Powder (IV) | 1 | 1 | 1 | 1 | 2 | 1 | 1 | 2 | 1 | 1 | 1 | 1 | 1 | 1 | 1 | 1.1 |
| Reference | 4 | 4 | 4 | 4 | 4 | 4 | 4 | 4 | 4 | 4 | 4 | 4 | 4 | 4 | 4 | 4.0 |

Testing Example 3

As a bad smell solution, a 0.05% solution of methylmercaptan in benzene, an aqueous 0.1% solution of trimethylamine and an aqueous 0.5% ammonia solution were provided. An aqueous 3% solution of the powder (I) or (II) obtained in Example 1 was adjusted to pH 7.0 with 2N sodium hydroxide. Each of these solutions was used as a sample solution.

Each 0.1 ml of the aforesaid bad smell solutions and 1 ml of the sample solution were put in a 1.5 ml-volume vial, which was then sealed. As a reference, the same volume of distilled water was put instead of the sample solution in a vial, which was then sealed. After shaken by a touch mixer for 20 seconds, the whole amount was put in a 300 ml-volume Erlenmeyer flask, 15 which was then sealed tightly with parafilm®. After the flask was incubated at 30° C. for one hour to attain a saturated state, a gas concentration in the head space was determined using a gas detecting tube for the detection of each bad smell (for methylmercaptan, No.71; for amines, No.180; and for ammonia, NoLa, ex Gastec Company). A bad smell removal was determined as a ratio in percentage of the decrease in the gas concentration to the gas concentration in the reference, distilled water.

TABLE 4

| Type of the bad smell substance | | Gas concentration, ppm | Removal, % |
|---|---|---|---|
| Metylmercaptan | Powder (I) | 8 | 70.4 |
| | Powder (II) | 5 | 81.5 |
| | Reference | 27 | |
| Trimetylamine | Powder (I) | 2 | 93.3 |
| | Powder (II) | 1 | 96.7 |
| | Reference | 30 | |
| Ammonia | Powder (I) | 2 | 97.5 |
| | Powder (II) | 5 | 93.8 |
| | Reference | 80 | |

From Table 4, it is seen that the present deodorizing substance exhibits the excellent effect of removing the bad smell substances, i.e. trimethylamine which is a cause of a fish smell and ammonia which is a cause of feces and urine smells. In addition, it also exhibited the excellent bad smell-removal for methylmercaptan which is a sulfur compound.

Testing Example 4

Candies were prepared using the powder (II) obtained in Example 1 (2) in the composition indicated in Table 5. In a reference, the same volume of distilled water was used instead of the powder (II).

TABLE 5

| | Test Sample | Reference |
|---|---|---|
| Composition, % | | |
| Isomalt | 75.2 | 75.2 |
| Acidulant | 0.5 | 0.5 |
| Color additive | 0.1 | 0.1 |
| Powder (II) | 2.0 | — |
| Distilled water | 22.2 | 24.2 |

Isomalt (Palatinit®: trade name, ex Mitsui Sugar Co., Ltd.) was dissolved in distilled water and heated to a temperature of 180° C. to be concentrated. Then, the solution was cooled to 120° C., to which an acidulant (citric acid, ex Fuso chemical Industries Inc.), a coloring agent (yellow color TH-S, safflower color, ex T.Hasegawa Co., LTD.) and the powder (II) were added. After kneaded well, the mixture was molded in a mold so as to give a weight of 3 g per candy.

A deodorizing effect was determined as follows. That is, after each subject smoked a cigarette, Seven Star®, to leave 2 cm length from the base of its filter, he(she) tasted the aforesaid candy for 3 minutes and then crushed it with the teeth and swallowed it down in the next 1 minute. The subject was then subject to a sensory test of his(her) breath. The sensory test was carried out in a manner that fifteen panelists smelled the breath of the three subjects and one reference who had tasted the reference candy. The evaluation was carried out according to the 5-level evaluation standards indicated in Table 6. The results are as shown in Table 7.

TABLE 6

| Level in the Rating | Evaluation Standards |
|---|---|
| 0 | almost no detectable smell |
| 1 | barely detectable smell |
| 2 | immediately detectable smell |
| 3 | strong, bad smell |
| 4 | very strong, bad smell |

TABLE 7

| | Evaluation | | | | | | | | | | | | | | | |
| --- | --- | --- | --- | --- | --- | --- | --- | --- | --- | --- | --- | --- | --- | --- | --- | --- |
| | Panelists | | | | | | | | | | | | | | | |
| Sample | A | B | C | D | E | F | G | H | I | J | K | L | M | N | O | Average |
| Subject A | 1 | 1 | 1 | 1 | 0 | 1 | 1 | 2 | 0 | 1 | 1 | 1 | 0 | 1 | 1 | 0.9 |
| Subject B | 0 | 1 | 2 | 1 | 1 | 2 | 2 | 2 | 1 | 1 | 0 | 0 | 1 | 0 | 1 | 1.0 |
| Subject C | 1 | 1 | 1 | 1 | 1 | 1 | 1 | 1 | 0 | 2 | 1 | 1 | 0 | 1 | 1 | 0.9 |
| Reference | 3 | 3 | 4 | 3 | 3 | 4 | 4 | 4 | 3 | 3 | 3 | 3 | 2 | 3 | 3 | 3.2 |

From Table 7, it is seen that a cigarette smell is removed by tasting a candy to which the present deodorizing substance is added.

Testing Example 5

A dog food was prepared using the powder (I) obtained in Example 1 (1) in the composition indicated in Table 8. In a reference, the same volume of distilled water was used instead of the powder (I).

TABLE 8

| | Test Sample | Reference |
| --- | --- | --- |
| Composition, % | | |
| Minced beef and pork | 90.0 | 90.0 |
| Seasoning | 3.0 | 3.0 |
| Thickening agent | 1.0 | 1.0 |
| Stabilizing agent | 0.5 | 0.5 |
| Powder (I) | 1.0 | — |
| Distilled water | 4.5 | 5.5 |

The preparation of the dog food was carried out according to a conventional manner. Use was made of "seasoning base" K-120 liquid (an oceanic bonito type, ex Ajinomoto Co., Inc.) as a seasoning, carrageenan for pet foods (Biocar, ex Nippon Biocon Company) as a thickening agent and Kimitsuarugin (ex Kimitsu Chemical Industries Inc.) as a stabilizing agent.

The deodorizing effect was determined as follows. That is, three adult dogs were each fed on 200 g of the dog food twice a day. The dogs were fed on the reference food for first one week and then on the test sample for second one week and, further, on the reference food for third one week. Their feces were sampled on the first day, 8th day, 11th day, 15th day, 18th day and 22nd day and subjected to a sensory test.

The sensory test was carried out as follows. Ten grams of feces of the aforesaid dogs were sampled in a sampling bag (NIOIBUKURO BAG) and incubated at 37° C. for 30 minutes. Then, only one person who had a sharp nose carried out the sensory test. The elevation was carried out according to the 5-level elevation standards indicated in Table 9. The results are as shown in Table 10.

TABLE 9

| Level in the Rating | Evaluation Standards |
| --- | --- |
| 0 | almost no detectable smell |
| 1 | barely detectable smell |
| 2 | immediately detectable smell |
| 3 | strong, bad smell |
| 4 | very strong, bad smell |

TABLE 10

| | Evaluation | | |
| --- | --- | --- | --- |
| | Adult Dog A | Adult Dog B | Adult Dog C |
| 1st day (start feeding the reference) | 4 | 4 | 3 |
| 8th day (start feeding the test sample) | 4 | 3 | 3 |
| 11th day | 2 | 2 | 1 |
| 15th day (start feeding the reference) | 1 | 1 | 1 |
| 18th day | 3 | 3 | 2 |
| 22nd day | 4 | 4 | 3 |

From Table 10, it is seen that when an adult dog is fed on a pet food which contains the present deodorizing substance, its feces smell is removed after several days feeding. It is presumed that a bad smell of feces, particularly the smell derived from methylmercaptan or hydrogen sulfide, is deodorized in the stomach and intestines.

Testing Example 6

Mouthwash was prepared using the powder (II) obtained in Example 1 (2). One gram of the powder (II) was added and dissolved in 500 ml of distilled water. This solution was used as mouthwash. After a subject ate five pieces of commercially available Gyozas (fried dumpling stuffed with minced pork and vegetables) containing garlic, he(she) rinsed his(her) mouth with 60 ml of the mouthwash three times. Three liters of his(her) breath was then sampled in a sampling bag. A reference ate the Gyozas as well and then rinsed his(her) mouth with distilled water instead of the mouthwash three times.

A sensory test was carried out by 15 panelists and was evaluated according to the 5-level evaluation standards indicated in Table 11 below. The results are as shown in Table 12.

TABLE 11

| Level in the Rating | Evaluation Standards |
| --- | --- |
| 0 | almost no detectable smell |
| 1 | barely detectable smell |
| 2 | immediately detectable smell |
| 3 | strong, bad smell |
| 4 | very strong, bad smell |

TABLE 12

| | Evaluation Panelists | | | | | | | | | | | | | | | |
|---|---|---|---|---|---|---|---|---|---|---|---|---|---|---|---|---|
| Sample | A | B | C | D | E | F | G | H | I | J | K | L | M | N | O | Average |
| Powder (II) | 1 | 2 | 1 | 2 | 3 | 2 | 1 | 2 | 1 | 2 | 1 | 2 | 1 | 1 | 1 | 1.5 |
| Reference | 4 | 4 | 4 | 4 | 4 | 4 | 3 | 4 | 4 | 4 | 4 | 4 | 4 | 3 | 4 | 3.9 |

From Table 12, it is seen that the mouthwash containing the present deodorizing substance exhibits a high deodorizing effect in the breath immediately after one eats a garlic.

Testing Example 7

Aerosol was prepared using the powder (II) obtained in Example 1 (2) by mixing the ingredients in the blend ratios indicated in Table 13. In a reference, the same volume of distilled water was used instead of the powder (II).

TABLE 13

| | Test Sample | Reference |
|---|---|---|
| Composition, % | | |
| Powder (II) | 20.0 | — |
| Ethanol | 65.0 | 65.0 |
| Distilled water | 15.0 | 35.0 |

As a bad smell solution, a 0.1% solution of methylmercaptan in ether, an aqueous 0.1% solution of trimethylamine and an aqueous 2% ammonia solution were used. After each 0.5 ml of the bad smell solution was put in a sampling bag having a volume of 3 liters and incubated at 30° C. for 2 hours, the aforesaid aerosol was sprayed from a spraying orifice into the bag for 4 seconds. The bag was sealed. After ten minutes, the gas concentration in the head space was determined using a gas detecting tube for the detection of each bad smell (for methylmercaptan, No.71; for amines, No.180; and for ammonia, No.3La, ex Gastec Company). A bad smell removal was determined as a ratio in percentage of the decrease in the gas concentration to the gas concentration in the reference.

TABLE 14

| Type of the bad smell substance | | Gas concentration, ppm | Removal, % |
|---|---|---|---|
| Metylmercaptan | Powder (II) | 10 | 73.0 |
| | Reference | 37 | |
| Trimetylamine | Powder (II) | 5 | 91.7 |
| | Reference | 60 | |

TABLE 14-continued

| Type of the bad smell substance | | Gas concentration, ppm | Removal, % |
|---|---|---|---|
| Ammonia | Powder(II) | 10 | 91.1 |
| | Reference | 112 | |

From Table 14, it is seen that the aerosol containing the present deodorizing substance exhibits an excellent effect of removing a bad smell of methylmercaptan, trimethylamine or ammonia.

Testing Example 8

A deodorizing test was carried out on canned short-necked clams using the powders (I) and (II) obtained in Example 1 and the powder (IV) obtained in Example 2. 50 g of the short-necked clams boiled in water (ex Inaba Foods Company) and 1 ml of an aqueous 0.1% solution of each of the aforesaid powders were put in a 100 ml beaker and mixed well. After the beaker was sealed with parafilm® and permitted to stand for 30 minutes, the beaker was opened and the short-necked clams boiled in water was eaten to examine its flavor. In a reference, the same volume of distilled water was used instead of the aforesaid solution of the powders. A sensory test was carried out by 15 panelists A to O, with the 5-level rating as indicated in Table 15 below. The results are as shown in Table 16.

TABLE 15

| Level in the Rating | Evaluation Standards |
|---|---|
| 0 | A fishy smell of short-necked clam can be hardly detected. |
| 1 | A fishy smell of short-necked clam can be barely detected. |
| 2 | A fishy smell of short-necked clam can be immediately detected. |
| 3 | A fishy smell of short-necked clam can be strongly detected. |
| 4 | A fishy smell of short-necked clam can be very strongly detected. |

TABLE 16

| | Evaluation Panelists | | | | | | | | | | | | | | | |
|---|---|---|---|---|---|---|---|---|---|---|---|---|---|---|---|---|
| Sample | A | B | C | D | E | F | G | H | I | J | K | L | M | N | O | Average |
| Powder (I) | 2 | 1 | 2 | 1 | 2 | 1 | 1 | 1 | 2 | 1 | 1 | 2 | 2 | 2 | 1 | 1.5 |
| Powder (II) | 1 | 1 | 2 | 2 | 2 | 1 | 1 | 1 | 1 | 2 | 1 | 1 | 1 | 1 | 1 | 1.3 |

TABLE 16-continued

| | Evaluation | | | | | | | | | | | | | | | |
|---|---|---|---|---|---|---|---|---|---|---|---|---|---|---|---|---|
| | Panelists | | | | | | | | | | | | | | | |
| Sample | A | B | C | D | E | F | G | H | I | J | K | L | M | N | O | Average |
| Powder (IV) | 1 | 2 | 3 | 1 | 1 | 2 | 2 | 1 | 2 | 1 | 2 | 2 | 2 | 1 | 1 | 1.6 |
| Reference | 3 | 4 | 4 | 3 | 3 | 3 | 4 | 3 | 4 | 3 | 4 | 4 | 4 | 3 | 4 | 3.5 |

From Table 16, it is seen that a fishy smell of short-necked clam is removed in the short-necked clams boiled in water to which the present deodorizing substance is added.

Industrial Applicability

The present deodorizing substance is effective for deodorizing a bad smell substance such as methylmercaptan, trimetylamine and ammonia. It is inexpensive and has high safety. Therefore, it maybe used advantageously, for instance, in foods, feeds, sanitary goods, table luxuries, medicines and quasi-drugs and useful in the fields of foods and environmental protection.

What is claimed is:

1. A method of deodorizing an object or area which comprises administering to the object or area an effective amount of a deodorizing substance obtained by treating a raw material by column chromatography, wherein the substance comprises a fraction obtained by the steps of:

(a) passing raw material selected from the group consisting of sugar cane juice and sugar cane-derived molasses through a chromatography column packed with a synthetic adsorbent as a fixed carrier, and (b) eluting ingredients absorbed on said synthetic absorbent with a solvent selected from the group consisting of water, methanol, ethanol and a mixture thereof, to produce a deodorizing substance, the deodorizing substance having a sugar content of not more than 50% by weight based on solid content.

2. The method of claim 1, wherein the synthetic adsorbent is an organic resin and the solvent is an ethanol-water mixed solvent.

3. The method of claim 1, wherein the synthetic adsorbent is an organic resin and the solvent is a mixed solvent of ethanol and water in a volume ratio of 50/50 to 60/40.

4. The method of claim 1, wherein the synthetic adsorbent is an aromatic resin and the solvent is a mixed solvent of ethanol and water in a volume ratio of 50/50 to 60/40.

5. The method of claim 1, wherein the synthetic adsorbent is an unsubstituted aromatic resin and the solvent is a mixed solvent of ethanol and water in a volume ratio of 50/50 to 60/40.

6. The method of claim 1, wherein the treatment by column chromatography is carried out by passing the raw material, at a column temperature of 60 to 97° C., through a column packed with an unsubstituted aromatic resin of a wet volume 0.01 to 5 times as much as a solid content of the raw material, and then eluting the ingredients adsorbed in the column at a column temperature of 20 to 40° C. with a mixed solvent of ethanol and water in a volume ratio of 50/50 to 60/40, and wherein the substance is in fractions in a range where a volume of the eluted solution collected since the start of the elution with the ethanol-water mixed solvent is at most 4 times as much as the wet volume of the aforesaid resin.

7. The method claimed in any one of claims 1 to 6, wherein a total amount of sucrose, glucose and fructose contained is not more than 50% by weight, based on a solid content.

8. The method claimed in any one of claims 1 to 6, wherein a total amount of sucrose, glucose and fructose contained is not more than 20% by weight, based on a solid content.

9. The method claimed in any one of claims 1 to 6, wherein a total amount of sucrose, glucose and fructose contained is not more than 5% by weight, based on a solid content.

* * * * *